United States Patent
Fox (10) Patent No.: US 6,942,775 B1
(45) Date of Patent: Sep. 13, 2005

(54) VERTICAL ELECTROPHORESIS SYSTEM

(75) Inventor: Gregory S. Fox, North Reading, MA (US)

(73) Assignee: Owl Separation Systems, Inc., Portsmouth, NH (US)

( * ) Notice: Subject to any disclaimer, the term of this patent is extended or adjusted under 35 U.S.C. 154(b) by 496 days.

(21) Appl. No.: 10/155,275

(22) Filed: May 24, 2002

(51) Int. Cl.$^7$ .................. G01N 27/26; G01N 27/447
(52) U.S. Cl. .............. 204/467; 204/456; 204/465; 204/466; 204/469; 204/470; 204/606; 204/615; 204/616; 204/618; 204/619; 204/620
(58) Field of Search .................. 204/456–470, 204/606–621; 264/261

(56) References Cited

U.S. PATENT DOCUMENTS

| | | | |
|---|---|---|---|
| 3,980,540 A | | 9/1976 | Hoefer .................. 204/180 |
| 4,560,459 A | * | 12/1985 | Hoefer .................. 204/467 |
| 4,574,040 A | * | 3/1986 | Delony et al. .......... 204/606 |
| 4,954,236 A | | 9/1990 | Kushner et al. ........ 204/299 |
| 4,957,613 A | * | 9/1990 | Schuette ................. 204/618 |
| 5,709,788 A | | 1/1998 | Chen .................... 204/619 |
| 5,882,495 A | | 3/1999 | Garrels ................. 204/456 |
| 6,013,165 A | * | 1/2000 | Wiktorowicz et al. ... 204/456 |
| 6,162,342 A | | 12/2000 | Perez et al. ........... 204/619 |
| 2004/0045829 A1 | * | 3/2004 | Ingenhoven et al. .... 204/465 |

FOREIGN PATENT DOCUMENTS

| | | | |
|---|---|---|---|
| DE | 299 22 680 | | 3/2000 |
| WO | WO 94/29005 | * 12/1994 | .......... B01D/57/02 |
| WO | 98/52031 | 11/1998 | |
| WO | WO 98/52031 | 11/1998 | |
| WO | WO 00/47984 | 8/2000 | |
| WO | 02/21116 | 3/2002 | |

OTHER PUBLICATIONS

"CLP Mini2 Vertical Gel System" Conlab web site, admitted prior art.

"SERVA BlueVertical Slab Gel System 160/C", Serva web site, admitted prior art.

"Mini–PROTEAN 3 Electrophoresis System", Bio–Rad Laboratories web site, admitted prior art.

* cited by examiner

Primary Examiner—Nam Nguyen
Assistant Examiner—Jeffrey Barton
(74) Attorney, Agent, or Firm—Andrus, Sceales, Starke & Sawall, LLP (57) ABSTRACT

A plugging medium is used to block the bottom opening of cassettes for vertical electrophoresis in order to facilitate filling the cassettes with separation media. Cassettes can be filled within a vertical electrophoresis system in which electrophoresis is conducted without further manipulation of the cassettes. The system includes a frame assembly mounted on a base containing a basin for plugging solution. The cassette is mounted to the frame assembly in a substantially vertical position such that a bottom opening of the empty cassette resides below the rim of the basin. The plugging solution (e.g. agarose gel) forms a plug within the bottom of the cassette to contain the separation medium.

55 Claims, 9 Drawing Sheets

FIG. 15

VERTICAL ELECTROPHORESIS SYSTEM

FIELD OF THE INVENTION

The present invention relates to a system for containing separation media in a vertical electrophoresis system.

BACKGROUND OF THE INVENTION

Electrophoresis has proven to be an important and useful separation method for organic macromolecules such as proteins and nucleic acids. Separation occurs as the structure, size, shape or electrical charge of a molecule affects the relative mobility of the molecule through a viscous medium within an electrical field. The separation medium is typically a gel, but a viscous liquid can serve as a separation medium as well. Viscous liquids can be advantageous when separating very large macromolecules, viruses, or cells, or when rapid elution of the desired molecule from the separation medium is desired. However, heat produced during electrophoresis renders liquid media more susceptible than gels to distortion of the resultant separation pattern.

There are many ways to contain separation media for use in vertical electrophoresis systems, but all are limited to use with gelled separation media. Often, a casting device is used to prepare a gel-filled cassette. The gel-filled cassette is then removed from the casting device and placed in the vertical electrophoresis unit for use. In a typical casting device, the separation medium is prepared by pouring a gelling solution such as agarose or acrylamide into a cassette comprised of two plates offset by spacers, forming a mold with an open top and sealed bottom. When the gel-filled cassette is removed from the casting device and placed into the vertical electrophoresis unit, the top edge of the gel is typically exposed to an electrolyte solution in an upper buffer chamber of the unit and the lower edge of the gel is typically exposed to an electrolyte solution in a lower buffer chamber in the unit. When using agarose gel as a separation medium, the surface of the plates used in the cassette are usually treated or "frosted" to prevent the gel from slipping out of the cassette during electrophoresis. The spacers are typically flat narrow strips of a dielectric material that, when sandwiched between two plates with moderate force, form a liquid tight seal, thus serving as the sidewalls of the internal space within the cassette. Because side spacers do not interfere with the path of electric current across the separation medium, the side spacers remain in place during electrophoresis.

In order to contain the separation medium while it gels, physical blocking means are normally placed along the bottom of the cassette for filling. Because the bottom edge of the separation medium must be in electrical contact with an electrolyte-containing buffer solution when it is used in an electrophoresis unit, most physical blocking means are removed before the cassette is used in an electrophoresis unit. This requires additional manipulation of the cassette.

In many labs, empty cassettes are loaded manually. For example, a gasket or tape is used to seal the bottom opening of the empty cassette while the separation medium is poured into the cassette and allowed to gel. The tape or gasket is then removed prior to use in electrophoresis. Alternatively, some lab technicians use a bead of agarose the seal the bottom opening. Once the bead of agarose forms a solidified plug, the cassette is filled with separation medium. The cassette can then be used for electrophoresis as is. While manual methods are useful, they are cumbersome and require extensive manipulation. In addition, it is difficult to ensure the integrity of the bottom seal prior to filling the cassette when using manual techniques.

Manipulation of cassettes, whether prepared manually or using a casting device, prior to electrophoresis has several drawbacks. Manipulation complicates procedures in the laboratory thereby making tasks more difficult. Excessive or careless manipulation can also compromise the integrity of the cassette. For example, the risk of dropping or otherwise breaking a cassette increases with additional manipulation. When using gradient-type separation media, the integrity of the cassette is especially susceptible to manipulation even when cassettes are handled carefully. In addition, manipulation of cassettes increases the likelihood and amount of contamination from DNA and proteins that are carried on hands, gloves, and other surfaces. Another drawback of handling cassettes is that it increases the exposure of laboratory personnel to potentially hazardous chemicals such as acrylamide.

Another drawback with vertical electrophoresis methods is that most vertical systems are not well suited for large format gels. In other words, the cassettes for vertical systems are small compared to the separation area in a typical horizontal system. Many casting devices for vertical electrophoresis function by creating downward pressure on the glass plates to force the bottom of the cassette against a sealing gasket. Due to the amount of force required to achieve an effective seal, cassettes prepared using this type of casting device use relatively small glass plates in order to prevent cracking and breakage. Small cassettes are not acceptable for some specimens. For example, large separation areas are often required to adequately separate macromolecules in a complex mixture.

Some prior art systems cast the gel slab within the vertical electrophoresis unit. For example, in U.S. Pat. No. 5,709,788, Chen shows a system that casts a gel and conducts electrophoresis in a single enclosure. Chen uses air pressure to retain the gelling solution in the mold during polymerization of the gel. Then, the air pressure is released to allow an electrolyte solution to make contact with the gel. Chen's system is limited to electrophoresis applications using gelled media and cannot be used with viscous liquid media.

U.S. Pat. No. 5,882,495 issued to Garrels discloses another system that cast the gel and conducts electrophoresis in the same unit. Garrels teaches an electrophoresis platform that tilts between horizontal and vertical positions. An opening in the lower reservoir of the device is sealed with a reversible sealant, such as tape, during polymerization of the gelling solution. The reversible sealant (e.g., tape) is removed or cut prior to electrophoresis. The Garrels system is limited to use with gelled media.

SUMMARY OF THE INVENTION

The invention relates to the use of a plugging medium to seal the bottom opening of a cassette for a vertical electrophoresis system. In its preferred form, the plugging medium is a conductive gel, such as an agarose gel. In general, an empty cassette is suspended so that the bottom opening of the cassette is located below the rim of a basin. The basin is filled or partially filled with the conductive plugging solution to seal the bottom opening of the cassette. Then, the cassette is filled with separation medium. The conductive plug preferably remains in place in the cassette along with the separation medium for conducting electrophoresis.

One aspect of the invention pertains to a method for containing a liquid separation medium or a gelled separation medium within a cassette. The method involves sealing the bottom opening of the cassette with a plugging solution, as described above, with the bottom opening of the empty cassette being exposed within a basin for the plugging solution. As mentioned, it is preferred that the plugging solution be conductive and that the basin be an integral component of the vertical electrophoresis unit. In this manner, electrophoresis can be conducted after pouring the conductive plugging solution into the basin, and providing a separation medium and one or more samples, without manipulating the cassette or removing the plug prior to conducting electrophoresis. While the preferred plugging medium is a conductive gel, the plugging medium can take other forms such as copolymers or hot melt doped with carbon or other suitable material to provide electrical conductivity, or high-density conductive liquids (e.g., glycerol) depending on the application.

The invention is well suited for containing both gel and liquid separation media in cassettes for vertical electrophoresis. The invention is also well suited for large formats because sealing is not dependent on pressure being exerted on the cassette plates. In addition, the invention eliminates the need to treat the inner surfaces of the plates when using agarose gel as the separation medium.

In another aspect, the invention is a vertical electrophoresis system having an integral basin for receiving the bottom opening of one or more cassettes and for holding the plugging solution, such that the cassette(s) can be loaded with separation media and electrophoresis conducted without manipulation of the cassette(s) prior to performing electrophoresis. In the preferred system, each cassette comprises two spaced plates that are clamped to a frame assembly. The frame assembly preferably has two stanchions extending upward from a base. The basin for the plugging solution is contained in the top surface of the base. The cassette is suspended from the frame assembly so that the bottom edges of the spaced plates are below the rim of the basin. It is preferred that the bottom opening be suspended above the floor of the basin a sufficient distance to ensure that the plugging solution has full access to the bottom opening. This is accomplished best by providing steps in the basin for supporting the bottom edge of the plates.

The frame assembly preferably fits within a lower buffer chamber to facilitate electrophoresis. An upper buffer chamber is defined by an internal space between cassettes or between a cassette and a spacer plate when a single cassette is used in a multiple cassette system or between a cassette and a back wall of the frame assembly in a single cassette system. The frame assembly also includes anode and cathode electrodes. A cover fits over the frame assembly to prevent accidental contact with electrical current during electrophoresis. The cover preferably provides connecting wires for the electrodes. Also, preferably, the system includes a heat exchanger to cool electrolyte solution in the upper buffer chamber during electrophoresis so that liquid media and large format separation media may be used without the detrimental effects of heat distortion.

In another embodiment, the invention contemplates the use of a basin remote from the electrophoresis unit and a conductive or non-conductive plugging solution. For example, the basin could be located in a casting device or the like. When the plugging solution is non-conductive, the plug must be removed after the separation medium has gelled. Manipulation of the cassette is required when the basin is remote from the electrophoresis unit whether using a fixed-conductive plug or a removable plug. Nevertheless, even in this embodiment, the invention tends to reduce the amount of manipulation and also leads to more consistency in cassette preparation.

BRIEF DESCRIPTION OF THE DRAWINGS

FIGS. 9–13 is a series of views similar to FIG. 5. More specific descriptions are provided below.

DETAILED DESCRIPTION OF THE INVENTION

Figures 1, 2:
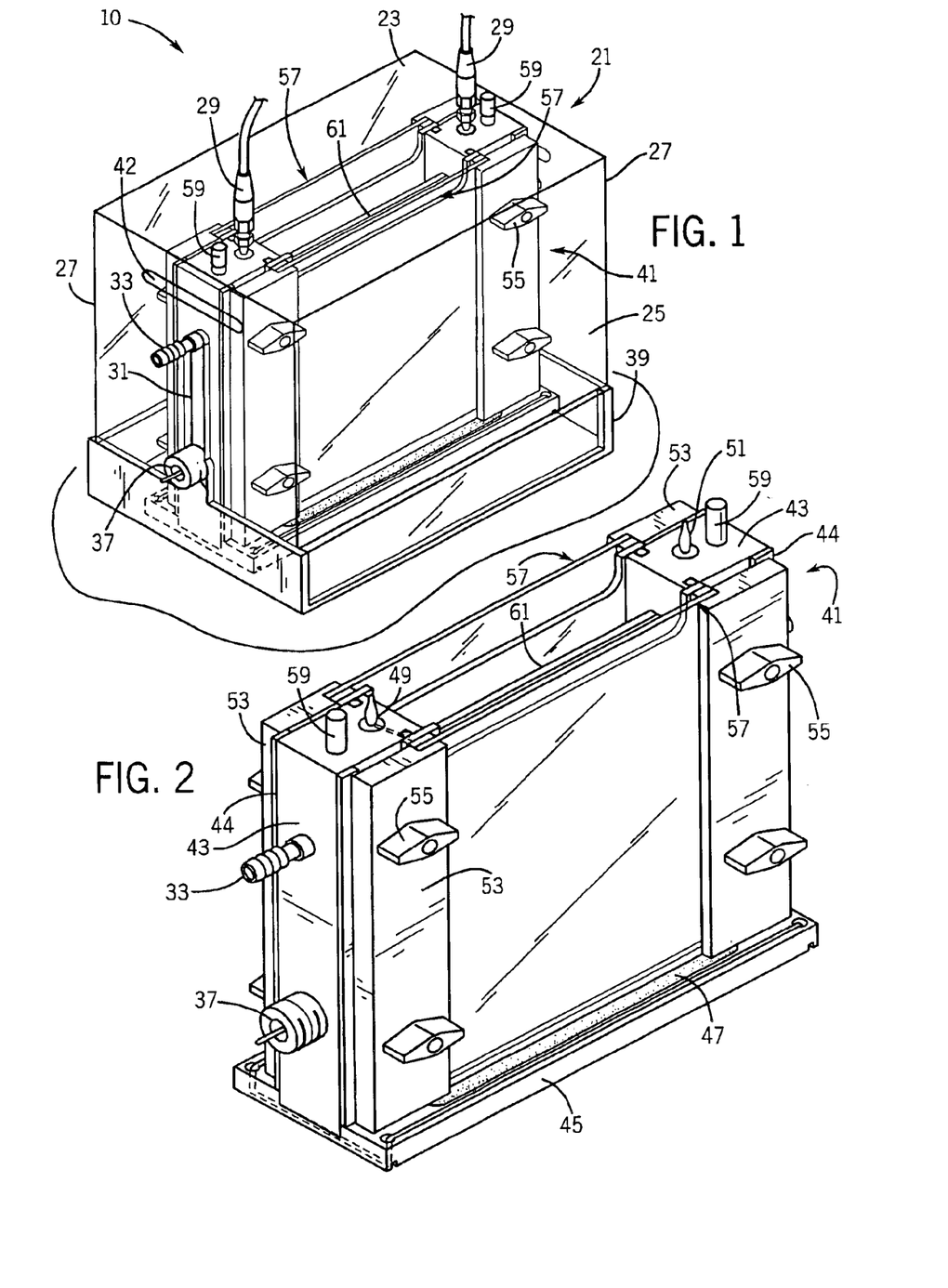
FIG. 1 is a perspective view of a system constructed in accordance with one embodiment of the invention.
FIG. 2 is a perspective view of a frame assembly in the system shown in FIG. 1, further showing two cassettes for containing separation media.

FIG. 1 is a perspective view of a vertical electrophoresis system (10) constructed in accordance with one embodiment of the invention. Referring to FIG. 1, the system (10) includes a cover (21) with a top surface (23), two longitudinal vertical surfaces (25), and two side surfaces (27). The cover (21) is preferably made of transparent plastic, such as polymethylmethacrylate, molded or machined, to accommodate the openings and fittings shown in the drawings. The cover (21) rests upon a wall of a lower buffer chamber (39), also preferably constructed of polymethylmethacrylate. Contained within the cover (21) and lower buffer chamber (39) is a frame assembly (41) for holding at least one cassette (57). In FIG. 1, the frame assembly (41) is holding two cassettes (57).

Electrical leads or connections (29) are attached to the top surface (23) of the cover (21) to receive a cathode electrode (49, FIG. 2) and an anode electrode (51, FIG. 2), respectively. Preferably, the location of the connections (29) for the electrodes are offset in such a way that the cover (21) will fit on the system (10) only if properly aligned to maintain the appropriate polarity of the anode (51) and cathode (49). Each side surface (27) of the cover (21) contains a slot (31) that fits over an inlet port (33) for a heat exchanger (61) on one side, and an outlet port (35) for the heat exchanger (61) on the other side. A pressure relief valve (37) for the heat exchanger (61) also passes through the slot (31) for the inlet port (33). Preferably, each side surface (27) of the cover (21) also contains a horizontal indentation (42), or alternatively a ridge, to facilitate finger placement and grip when removing the cover (21). The frame assembly (41) preferably has upwardly extending posts (59) that pass through corresponding holes in the cover (21). These posts (59) serve as thumb placement sites for exerting an opposing force to facilitate lifting of the cover (21).

FIG. 2 is a perspective view of the preferred frame assembly (41) with two cassettes (57) attached. In FIG. 2, the frame assembly (41) and cassettes (57) are located outside of the lower buffer chamber (39) and the cover (21). The frame assembly (41) has a vertical member (43) and a platform-style base (45). As described in more detail below, the vertical member (43) is a generally U-shaped member having a pair of stanchions (44). The U-shaped vertical member (43) is mounted on to the base (45) such that the stanchions (44) extend upward from the base (45). The base (45) contains a basin (47) in its top surface. Preferably, the base (45) and the vertical member (43) of the frame assembly are molded or machined as separate components. Polymethylmethacrylate is a preferred material for the vertical member (43). Normally, it should be sufficient to attach the vertical member (43) to the base (45) through solvent bonding. In the embodiment of the invention shown in the drawings, the frame assembly includes one vertical member (43), although it is possible, in accordance with the invention, for the system (10) to have more than one vertical member (43).

Referring still to FIG. 2, a cathode electrode (49) is located on the top surface of one of the stanchions (44) of the U-shaped vertical member (43). An anode electrode (51) is located on the top surface of the other stanchion (44) of the U-shaped vertical member (43). Clamping mechanisms (53) are attached to the front faces (144, FIG. 3) and rear faces (143, FIG. 4) of each stanchion (44). The clamping mechanisms (53) hold the cassettes (57) in position on the frame assembly (41). In the preferred embodiment, the clamping mechanisms (53) consist of molded and/or machined plastic runners held in place by knobbed nuts (55) fastened to screws (56) embedded in the stanchions (44). One skilled in the art will appreciate that other devices can be used to clamp the cassettes (57) in place.

Figure 3:
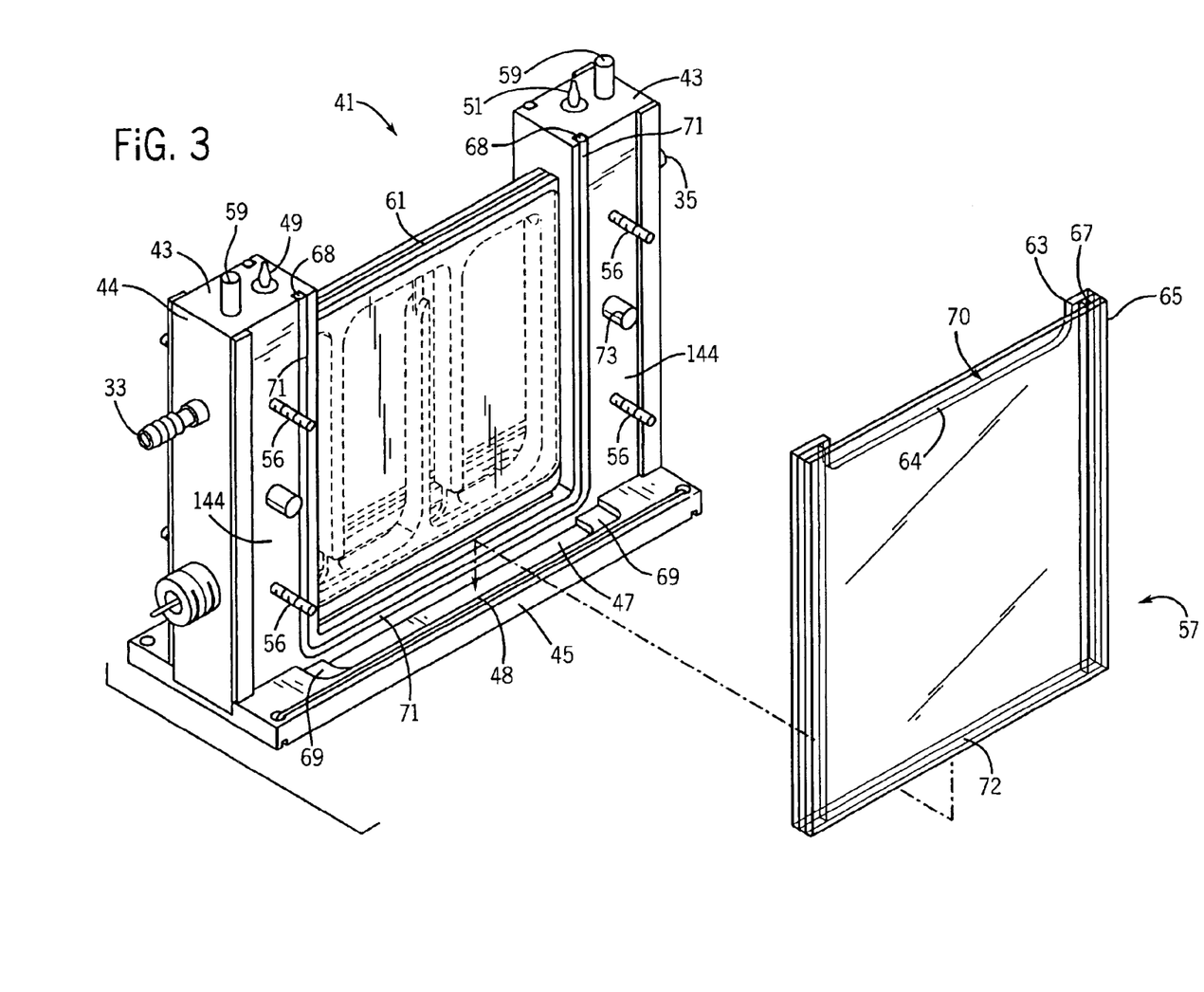
FIG. 3 is a view, similar to FIG. 2, showing the cassette exploded from its position on the frame assembly.

Referring now to FIG. 3, each cassette (57) is preferably constructed from a two plates (63) and (65). Both plates (63)(65) are generally rectangular, except the first plate (63) has a longitudinal notch (64) along its top edge. The plates are separated by flat, narrow spacers (67) made of dielectric material such as rigid polyvinyl chloride or acetal material. For thin gels, polyester is a preferred material for the spacers (67). The spacers (67) seal the sides of the cassette (57) when moderate pressure is applied. Normally, the spacers (67) keep the plates (63) and (65) parallel to one another with a spread selected for a particular application. Typical thicknesses for spacers (67) range from 0.03 inches to 0.125 inches. The plates of the cassette (57) are preferably glass, however, transparent plastic or another suitable material may be used. Although each empty cassette (57) has sealed sides, each cassette (57) has a top opening (70) and a bottom opening (72) between the first (63) and second (65) plates.

Each cassette (57) is placed in a substantially vertical position on the frame assembly (41) with the notched first plate (63) facing inwardly. The bottom opening (72) of the cassette (57) sits below the rim (48) of the basin (47) in the base (45) of the frame assembly (41). Preferably, the cassette (57) rests on one or more steps (69) located within the basin (47), and more preferably, the steps (69) are located at each end of the basin (47) underneath the location where the spacers (67) would normally be located. The floor (50) of the basin (47) is generally flat but for the steps (69). Preferably, the depth of the basin is about 0.25 inches. The preferred step height is about 0.13 inches, and when multiple steps are used, each step is preferably the same height. This configuration is especially useful because it assures reliable loading of the cassette (57) into the frame assembly (41). Other ways of guiding a cassette (57) can be used within the spirit of the invention. For example, a placement mark on the cassettes (57) or frame assembly (41), or a stand-off centrally located in the basin (47), can be used. Also, the invention can be implemented without providing means for guiding the placement of a cassette (57) with respect to the height of the basin floor (50) and/or rim (48). The structure of the base (45) is shown and described in more detail in connection with FIG. 6.

Still referring to FIG. 3, both the front face (144) and the rear face (143, FIG. 4) of the U-shaped vertical member (43) contain a U-shaped groove (68). A sealing gasket (71) is located in each U-shaped groove (68). The clamping mechanisms (53, FIG. 2) apply force against the cassette (57) to seal the cassette (57) along the U-shaped sealing gasket (71) on the frame assembly (41). This seal creates a fluid-tight internal space within the center of the frame assembly (41), which serves as an upper buffer chamber (72) as illustrated best in FIGS. 4 and 5. The addition of another cassette (57), or of a solid plate (not shown) in the absence of another cassette, to the other side of the frame assembly (41) completes the upper buffer chamber (72). Alternatively, the frame assembly (41) may be designed with a solid back wall in order to accommodate only a single cassette. Referring still to FIG. 3, the system (10) has a central integral heat exchanger (61), as shown in phantom, within the frame assembly (41). Heat conduction plates (84) abut each side of the heat exchanger (61).

Figure 4:
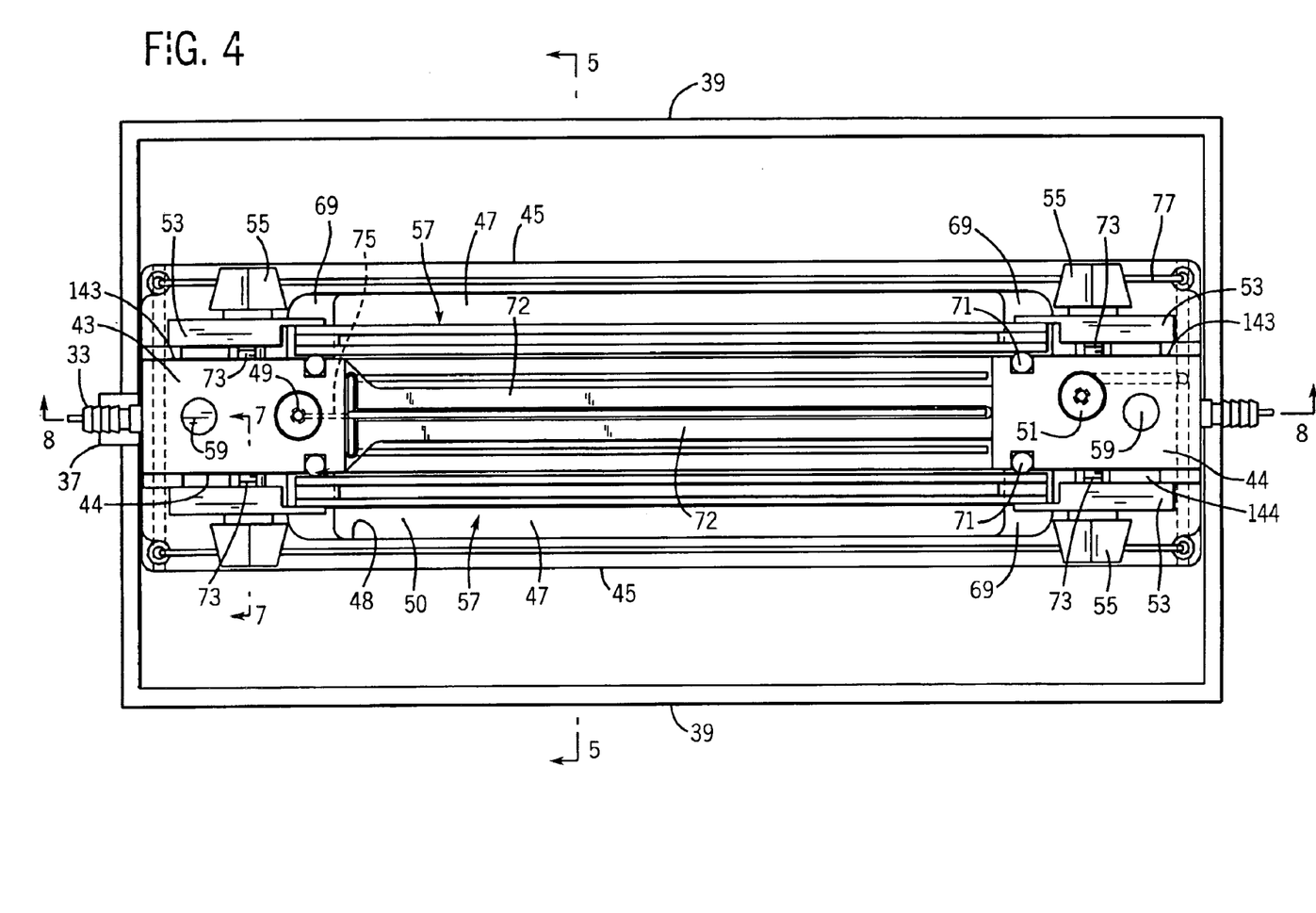
FIG. 4 is a top view of the system shown in FIG. 1, without the cover.

FIG. 4 shows a top view of the system (10) illustrated in FIG. I without the cover (21). The cathode electrode (49) and anode electrode (51) are shown on the top surface of the stanchions (44) of the vertical members (43) of the frame assembly (41). Thumb placement posts (59) are also shown on the top surface of the stanchions (44) of the vertical members (43). Likewise, FIG. 4 shows the ends of the U-shaped sealing gaskets (71) located in grooves (68) for sealing the cassettes (57) against the frame assembly (41). Clamping mechanisms (53) are also shown on each face of the two stanchions (44). FIG. 4 also depicts the base (45) with U-shaped vertical member (43) being mounted on the base (45) such that a separate basin (47) is formed for each cassette (57), on the respective side of the U-shaped vertical member (43). FIG. 4 also illustrates each cassette (57) resting upon the steps (69) in the respective basin (47).

Still referring to FIG. 4, the cathode electrode (49) is electrically connected to the upper buffer chamber (72) through one or more wires (75). The anode electrode (51) is wired to the base (45) through one or more wires (77). FIG. 4 also shows the central, integral heat exchanger (61) provided between the stanchions (44) within the U-shaped vertical member (43) of the frame assembly (41). The inlet port (33), outlet port (35) and pressure relief valve (37) are also shown.

Figure 5:
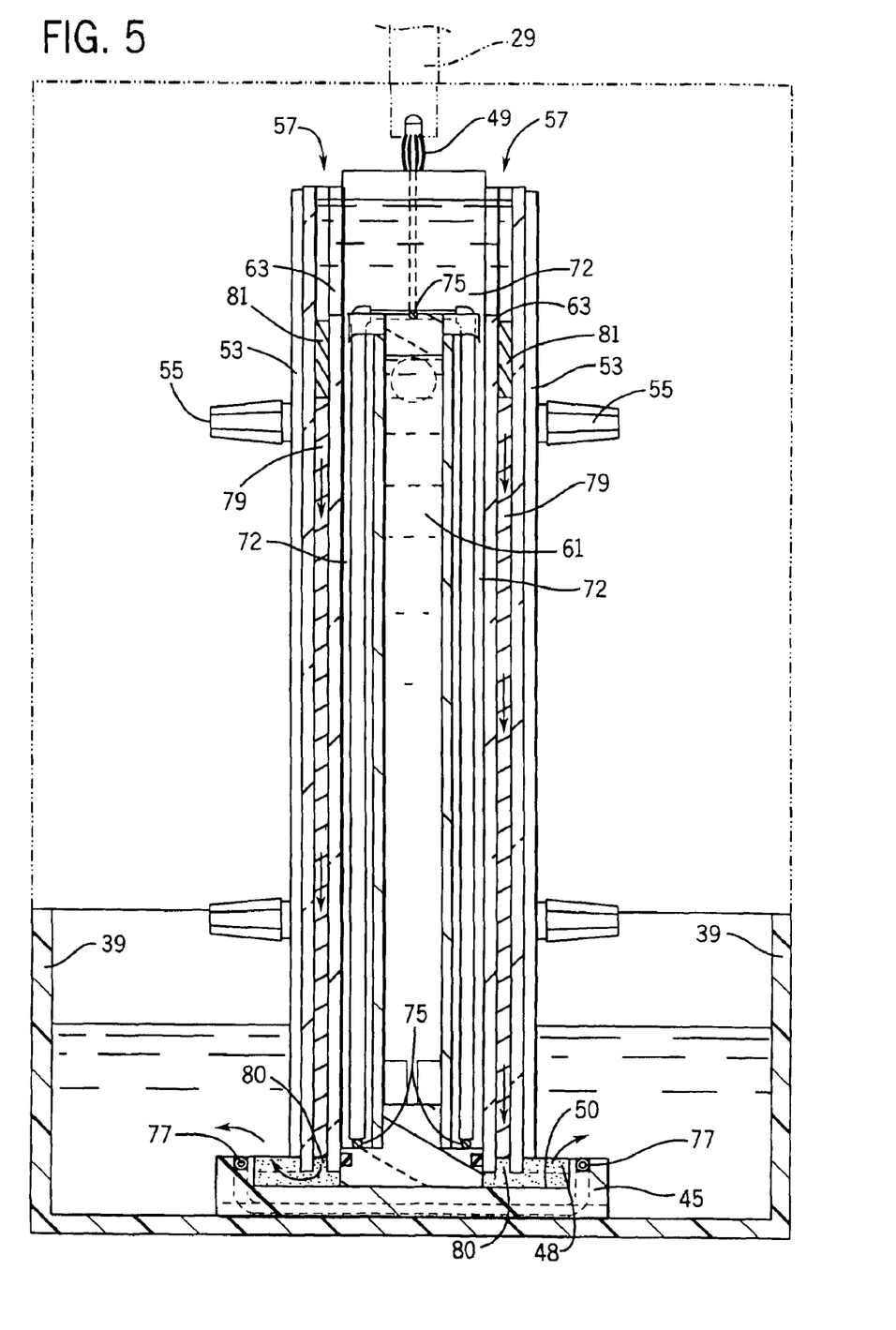
FIG. 5 is a view taken along line 5—5 in FIG. 4, showing the system fully loaded with separation media and sample specimens as is during electrophoresis.

FIG. 5 shows the system (10) from a perspective taken along line 5—5 in FIG. 4. In FIG. 5, various reagents are loaded into the system (10) and the system (10) is operating to conduct electrophoresis. The basin (47) on the top surface of the base (45) is filled with a plugging medium (78). The plugging medium (78) has flowed into the bottom opening (72) of the cassette (57) and formed a plug (80) between the plates at the bottom end of the cassettes. In the system (10) shown in the drawings, the plugging medium (78) is electrically conductive. Preferably, the plugging medium (78) is an agarose gel, which is poured into the basin (47) in the form of an aqueous solution of agarose of approximately 2% w/v. The solution seeks an even height throughout the basin (47), even within the portion of the cassette (57) that is submerged in the solution. When the agarose solidifies a gelled plug (80) is formed. While gelling solutions will normally be the preferred plugging medium, it should be apparent to one skilled in the art that the plugging medium (78) may take many forms. For example, the plugging solution may be an ethylene vinyl acetate copolymer or hot melt, doped with carbon to render it electrically conductive. Also, the plugging solution need not be capable of solidification and may remain in a liquid or semi-solid state. To serve as a liquid plugging solution, a liquid must be electrically conductive, must have a greater density than the electrolyte solution contained in the lower buffer chamber (39), and must offer a greater resistive force than the hydrostatic pressure provided by the separation medium at the height of the notched plate (63) in the cassette (57). One example of such a liquid is glycerol, but those skilled in the art will appreciate that other liquids may be substituted.

After the bottom of the cassette (57) has been plugged, a separation medium (79) is added to the cassette (57). Since different applications require different separation media, the skilled artisan will appreciate that any suitable medium, whether gelled or liquid may be used as long as it is capable of conducting an electric current. The frame assembly (41) can be placed into the lower buffer chamber (39) after the separation medium (79) is loaded or, preferably, before the separation medium (79) is loaded, and even more preferably before the plugging medium (78) is poured. Prior to electrophoresis, one or more samples (81) to be separated are placed on the top of the separation medium (79). One skilled in the art will understand that the sample (81) can be in liquid form or in solid form, such as a gel slice or impregnated filter. An electrolyte-containing solution is added to the upper buffer chamber (72) such that the solution makes contact with the top surface of the sample (81) on the top of the separation medium (79). Also, an electrolyte-containing solution is added to the lower buffer chamber (39). The lower buffer chamber (39) preferably has a fill-line indicator (not shown). In addition, the capacity of the lower buffer chamber (39) is preferably large enough to contain the volume of electrolyte solution up to the fill-line plus the volume of electrolyte solution in the upper buffer chamber (72) in the event of leakage from the upper buffer chamber (72). During electrophoresis, an electric current is passed from the electrolyte solution in the upper buffer chamber (72) through the sample (81), separation medium (79), and plugging solution into the electrolyte solution in the lower buffer chamber (39) as indicated by the arrows in FIG. 5.

Figures 6, 7:
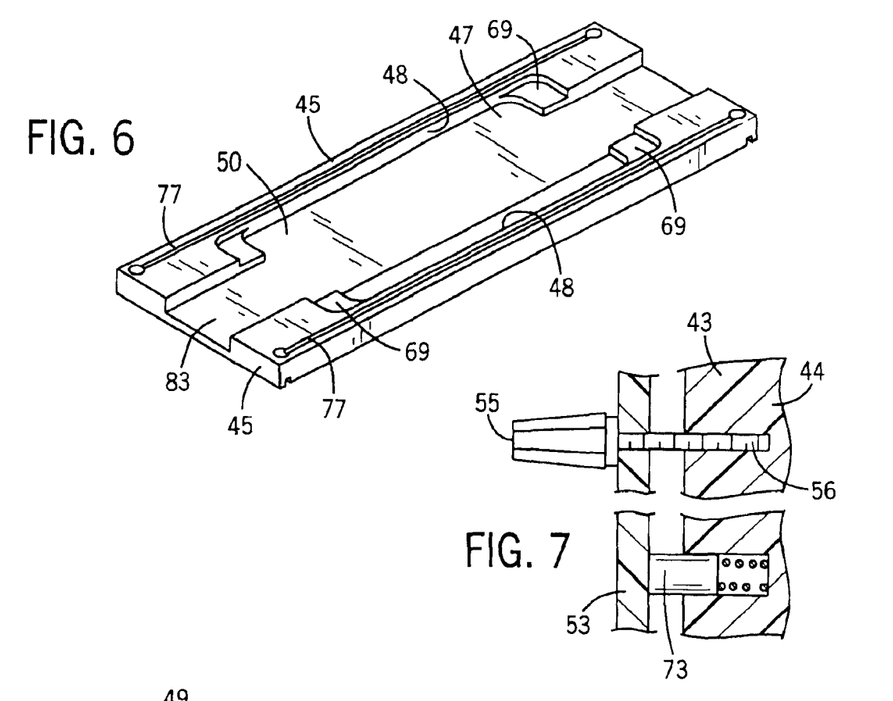
FIG. 6 is a perspective view of the base of the frame assembly shown in FIG. 2.
FIG. 7 is a detailed view taken along line 7—7 in FIG. 4 showing a clamp mechanism used to secure the cassette to the frame assembly.

FIG. 6 is a perspective view of the base (45) of the frame assembly (41) for the preferred system (10). The base (45) contains a central, longitudinal track (83) or depression into which the U-shaped vertical member (43) is mounted. As mention above, a basin (47) with steps (69) at each lateral end is provided on each side of the track (83). Alternatively, the base (45) may contain multiple tracks (83) for additional vertical members (43), or the base (45) may be designed for one-sided systems. FIG. 6 shows each basin (47) having steps (69) at each lateral end. The base (45) contains openings and grooves for wires (77) to make the electrical connection to the anode (51, FIGS. 2 and 15). In a preferred embodiment, the wires (77) run lengthwise along each side of the base (45) to facilitate contact with electrolyte solution in the lower buffer chamber (39). One skilled in the art will appreciate that the wiring arrangement may be varied as long as sufficient contact is made with the electrolyte solution contained in the lower buffer chamber (39).

FIG. 7 is a detailed view taken along line 7—7 in FIG. 4, of the preferred clamping mechanism (53) for holding a cassette (57) to the frame assembly (41). FIG. 7 shows the clamping mechanism (53) resting against a spring-biased peg (73). The spring-biased peg (73) pushes against the clamping mechanism (53) to hold it away from the stanchion (44) of the U-shaped vertical member (44) when the nut (55) is not tightened. This allows the cassette (57)(not shown in FIG. 7) to be easily placed or removed from the clamping mechanism (53).

Figure 8:
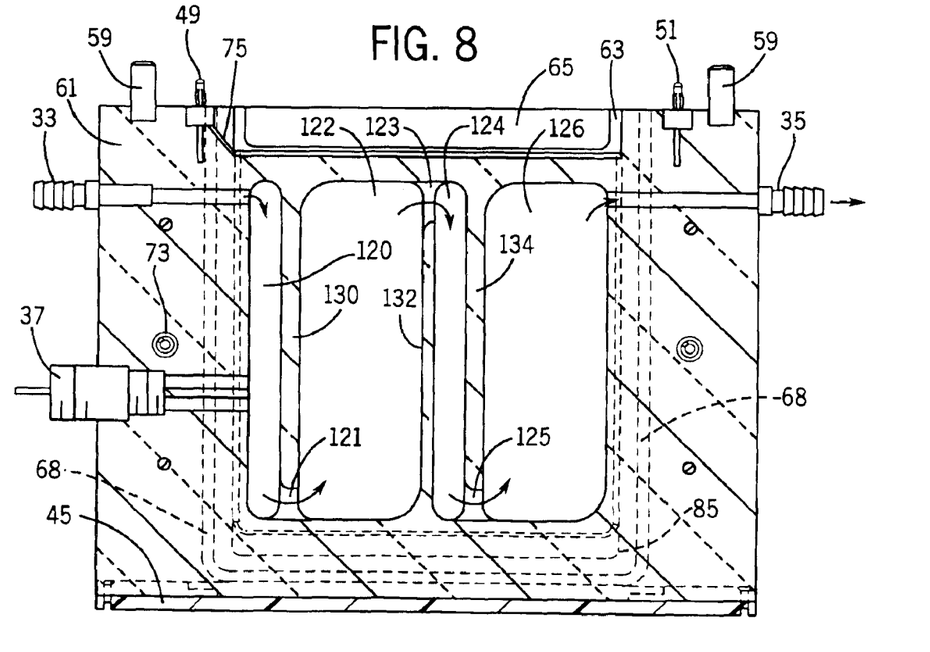
FIG. 8 is a detailed view taken along line 8—8 in FIG. 4 showing components of an internal heat exchanger in the system shown in FIG. 1.

FIG. 8 is a view taken along line 8—8 of FIG. 4 showing components of the heat exchanger (61). Although the system (10) shown in the drawings has a heat exchanger, depending upon the size and application of the system (10) a heat exchanger may not be required. Coolant flows into the heat exchanger (61) through the inlet port (33) and is released through the outlet port (35). In a preferred embodiment, the inlet port (33) is connected to a faucet providing cold tap water (not shown). The flow path (illustrated by arrows) of the integral heat exchanger (61) consists of a serpentine channel with repeating downturns and upturns. Each downturn and upturn leads to a subsequent flow chamber. The body of the heat exchanger (61) is made from machined plastic, preferably polymethylmethacrylate. The body is sandwiched between two heat-conductive, but electrically insulating plates (84) (see FIG. 3), preferably alumina plates or other type of ceramic plates. A set of dashed lines (85) in FIG. 8 indicates where the heat-conductive plate (84) may be seated. The other set of dashed lines indicates the groove (68) for the sealing gasket (71). Referring still to FIG. 8, the first cooling chamber (120) following the coolant inlet port (33) directs the coolant downward to a passageway (121) leading to a second cooling chamber (122). The second cooling chamber (122) directs the coolant upward to passageway (123) leading to a third cooling chamber (124). The third cooling chamber (124) directs the coolant downward to a passageway (125) leading to a fourth cooling chamber (126). The fourth cooling chamber (126) directs the coolant upward to the coolant outlet port (35). Cooling chambers (120), (122), (124), (126) are separated by baffles (132), (134), (136). The passageways (121), (123), (125) are machined through the baffles. The cooling chambers (120), (124) that follow a downturn are substantially smaller in volume than the cooling chambers (122), (126) that follow an upturn. This design allows the heat exchanger (61) to be filled completely without trapping air.

Figure 9:
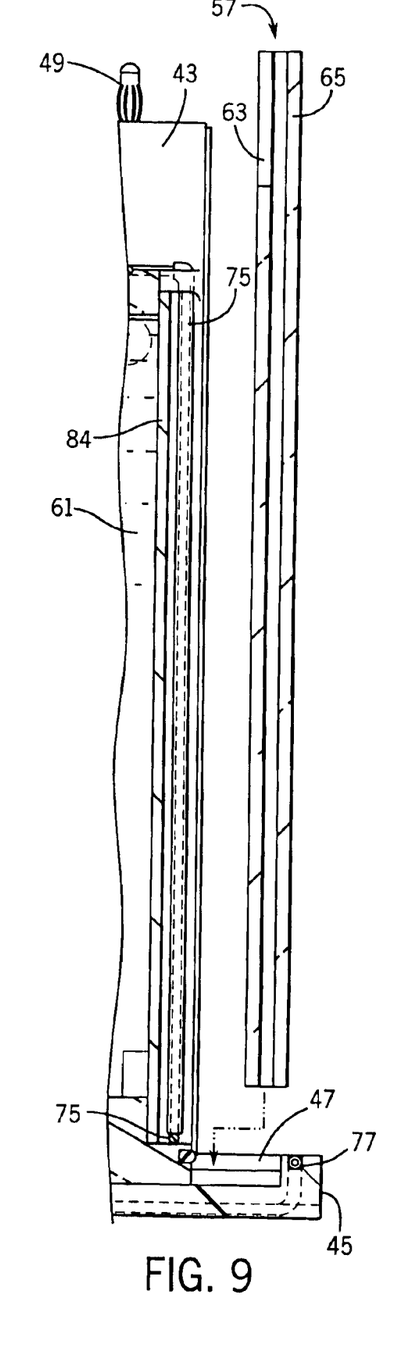
FIG. 9 shows an empty cassette before it is loaded onto the base of the frame assembly shown in FIG. 3.
Figure 10:
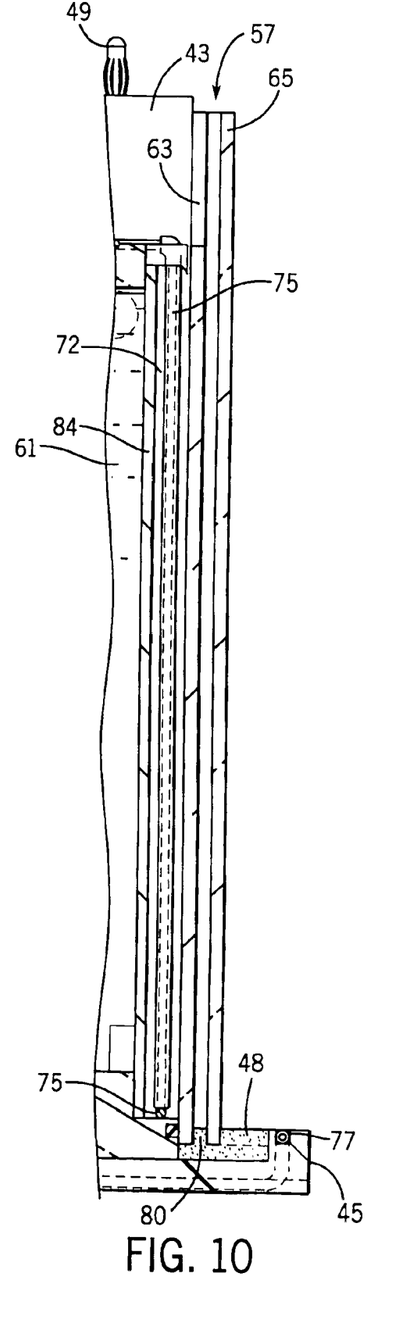
FIG. 10 shows the cassette in position and a plugging solution filling a basin in the base of the frame assembly to plug the bottom opening of the cassette.
Figure 11:
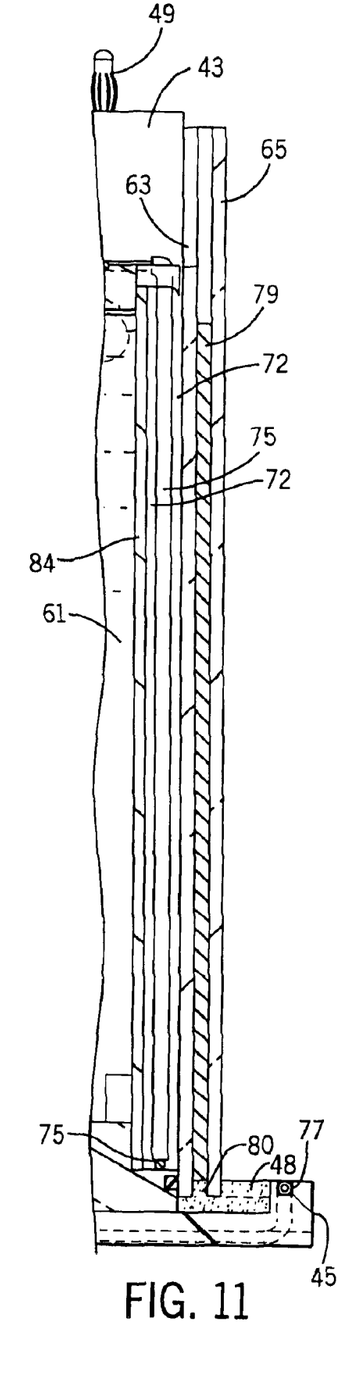
FIG. 11 shows the system in FIG. 10 with the addition of separation medium between the plates of the cassette.
Figure 12:
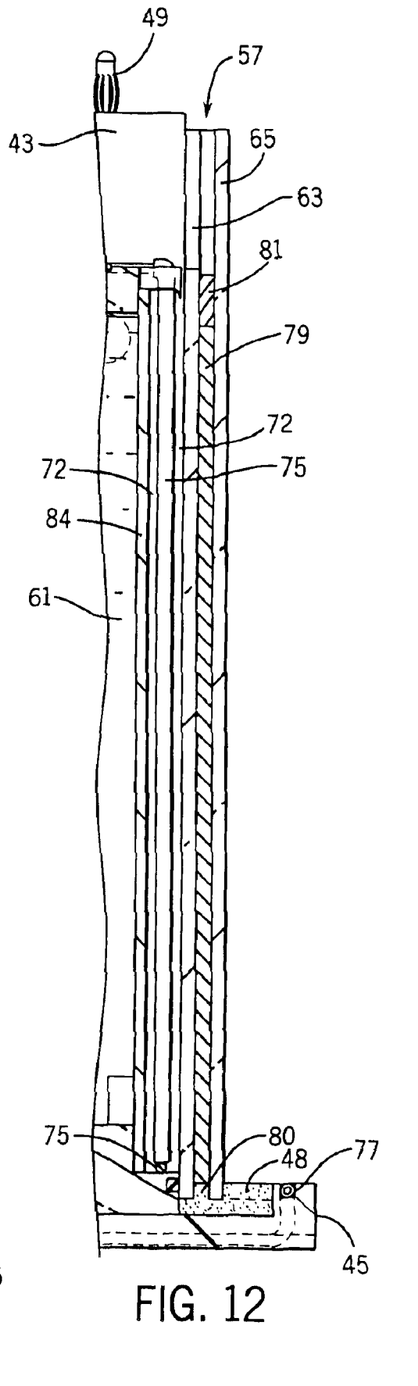
FIG. 12 shows a sample loaded on top of the separation medium.
Figure 13:
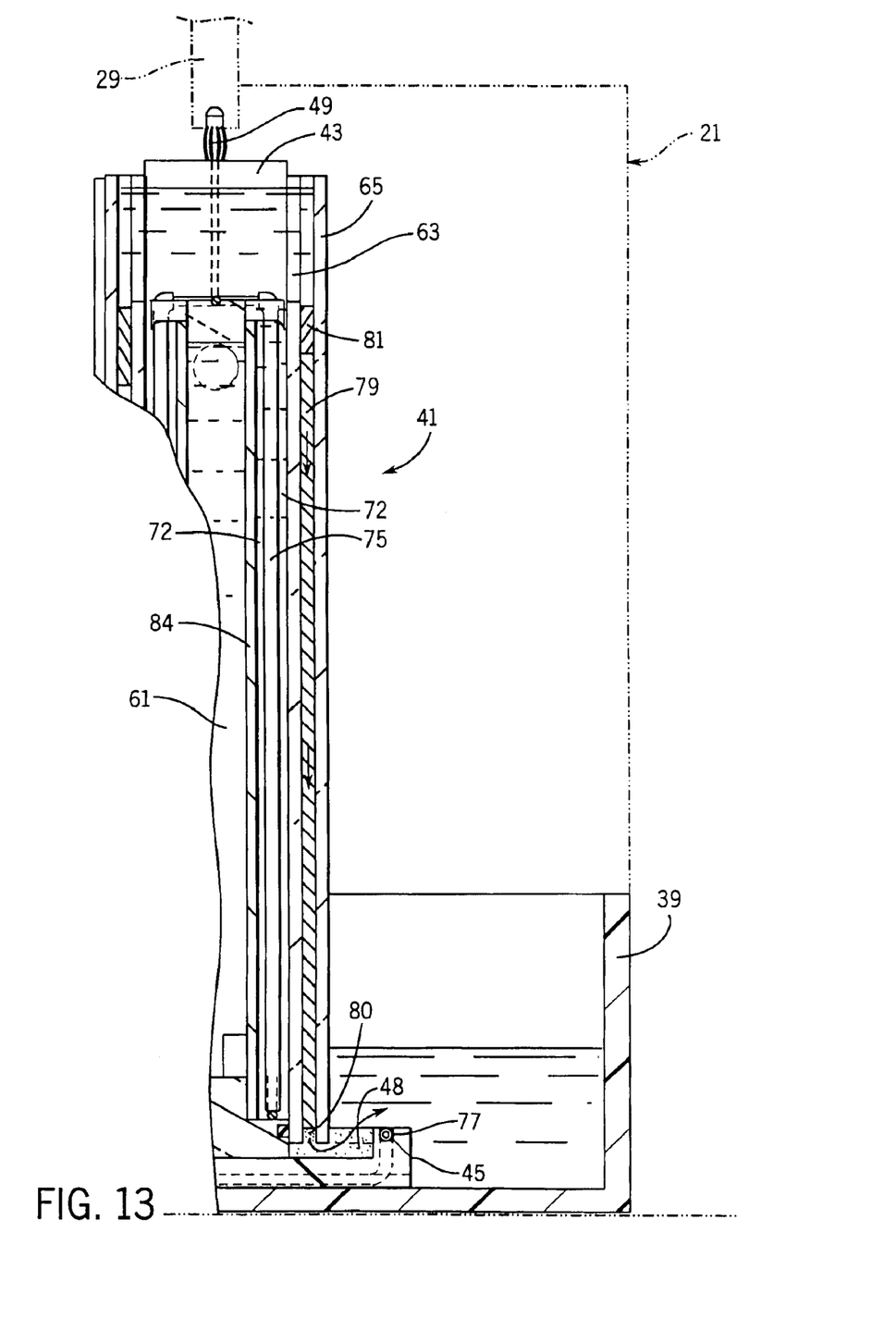
FIG. 13 illustrates the system in use for electrophoresis, namely an upper buffer chamber containing an electrolyte solution in contact with the sample, and the frame assembly sitting within a lower buffer chamber filled with an electrolyte solution to facilitate the creation of an electrical field vertically across the separation medium.

FIGS. 9 through 13 illustrate use of the preferred system (10). FIG. 9 is a view similar to that of FIG. 5 depicting one side of the frame assembly (41). FIG. 9 shows an empty cassette (57) before it is loaded onto the frame assembly (41) with the bottom of the cassette (57) placed within the basin (47) on the base (45) of the frame assembly (41). FIG. 10 is a sequential view following FIG. 9. FIG. 10 shows the cassette (57) loaded onto the frame assembly (41) and a plugging medium (78), as described in FIG. 5, poured into the basin (47). Note that the plugging medium (78) fills the space at the bottom of the cassette (57) to form a plug (80). FIG. 11 shows the next step in which a separation medium (79) is poured between the plates of the cassette (57). The separation medium (79) may be a liquid or a gel depending upon the application. Although not shown in FIG. 11, the frame assembly (41) is preferably placed within the lower buffer chamber (39) prior to pouring the separation medium (79). FIG. 12 shows the next step in which a sample (81) to be separated is placed on the top surface of the separation medium (79). FIG. 13 shows a fully loaded cassette (57) and frame assembly (41) placed within a lower buffer chamber (39). The sample (81) or samples on top of the separation medium (79) are contacted by a solution of electrolytes in the upper buffer chamber (72). The lower buffer chamber (39) also contains a volume of electrolyte solution, preferably regulated by a fill-line indicator.

Figure 14:
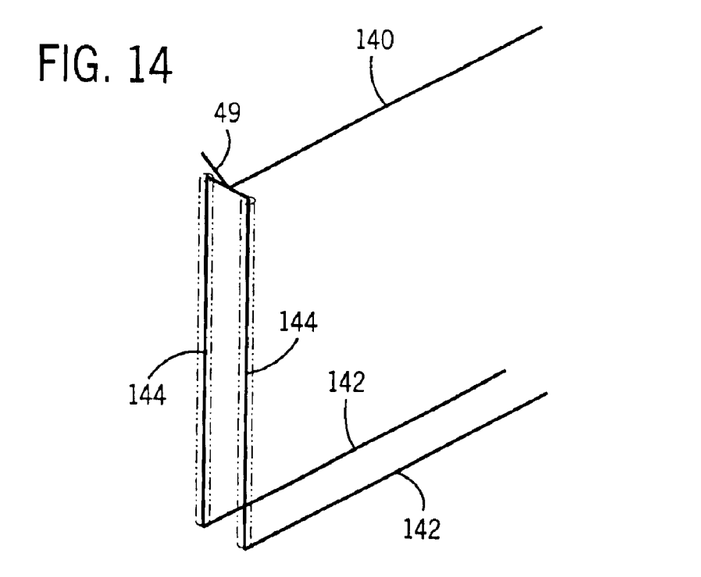
FIG. 14 is a schematic view of the wiring arrangement electrically connected to the cathode electrode in the system shown in FIG. 1.

FIG. 14 shows the preferred wiring arrangement (75) for the upper buffer chamber (72), which is electrically connected to the cathode electrode (49). Wires (140), (142) span across along the top and bottom regions of the U-shaped vertical member (43)(not shown) of the frame assembly in the pattern shown in FIG. 14. In this manner, the electrolyte solution in the upper buffer chamber (72)(not shown) carries a uniform, positively charged electrical current. The vertical wires (144) are preferably coated with an electrically insulating material so that only the horizontal wires (140), (142) are in electrical contact with the electrolyte-containing solution in the upper buffer chamber (72).

Figure 15:
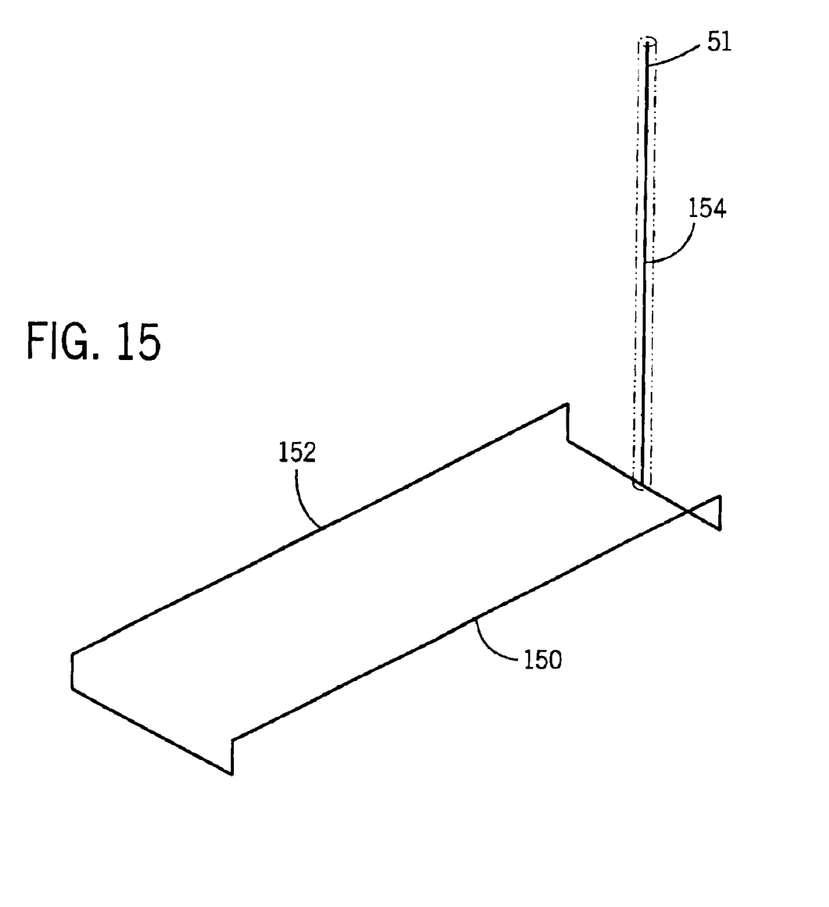
FIG. 15 is a schematic view of the wiring arrangement electrically connected to the anode electrode the system shown in FIG. 1.

FIG. 15 shows the preferred wiring arrangement (77) for the lower buffer chamber (39), which is electrically connected to the anode electrode (51). Wires (150), (152) span the base (45) of the frame assembly (41). The vertical wire (154) is preferably coated with an electrically insulating material. Those skilled in the art will appreciate that the wiring arrangement may be varied, as long as sufficient contact is made with the respective electrolyte solution.

The invention has been described herein with respect to a preferred embodiment of implementing the invention. It should be apparent to those skilled in the art that certain aspects of the invention may be useful in other forms. For example, elements of the frame assembly (41) as described herein, may be useful as a separate casting device. In this regard, the casting device would include a vertical member attached to a platform base as illustrated in FIGS. 5 and 6. In this embodiment, an empty cassette (57) is placed in a substantially vertical position on the frame assembly (41) such that the bottom opening (72) of the cassette (57) sits below the rim (48) of the basin (47) in the base (45) of the casting device. The basin (47) is then filled with the plugging medium (78). Once the plugging medium (78) solidifies, the separation medium (79) is poured between the plates while the cassette (57) remains mounted to the casting device. Then the loaded cassette (57) is removed from the casting device and placed in a vertical electrophoresis unit. One or more samples are then placed on top of the separation medium in the cassette and electrophoresis is conducted.

In this embodiment of the invention, it is preferred that the plugging solution be a electrically conductive gel. If the plugging solution is non-conductive, the separation medium must be a gel and the plug must be removed after the separation medium has solidified.

Other embodiments, modifications, improvements or alternatives may be apparent to those skilled in the art. Such embodiments, modifications, improvement or alternatives are considered to be within the spirit of the invention.

What is claimed is:

1. A system for containing at least one separation medium and for performing vertical electrophoresis within a single apparatus comprising:
    (a) at least one cassette for containing at least one separation medium, said at least one cassette comprising (i) a first plate and a second plate, (ii) a space for containing said separation medium between said first plate and said second plate of said cassette, said cassette having an open top and an open bottom;
    (b) a frame assembly for receiving said at least one cassette, the frame assembly having (i) at least one clamping mechanism for pressing said at least one cassette against said frame assembly in a substantially vertical position thereby forming a fluid-tight seal between said first plate and said frame assembly and defining at least one upper buffer chamber, (ii) a base comprising a platform extending beyond said at least one cassette when said cassette is clamped in position on said frame assembly, said base having at least one basin for receiving the open bottom of said at least one cassette and having a solution capable of plugging the bottom of said cassette, (iii) a first electrode for said upper buffer chamber, and (iv) a second electrode for a lower buffer chamber; and
    (c) a lower buffer chamber comprising a container for holding an electrolyte solution within which said base of said frame assembly is positioned.

2. The system of claim 1 wherein said first plate and said second plate are flat and generally rectangular.

3. The system of claim 1 wherein said first plate and said second plate are glass.

4. The system of claim 1 wherein said first plate and said second plate are at least 20 cm by 20 cm.

5. The system of claim 1 wherein said first plate bears a longitudinal notch along a top edge to facilitate contact between said separation medium and a solution of electrolytes.

6. The system of claim 1 wherein said first plate and said second plate are separated by two strips of dielectric material placed along each vertical side of said first plate and between said first plate and said second plate.

7. The system of claim 6 wherein said clamp mechanism also presses said first plate and said second plate together.

8. The system of claim 1 wherein said basin contains at least one step for keeping said at least one cassette off of the floor of said basin.

9. The system of claim 8 wherein said at least one step is located centrally within said basin.

10. The system of claim 1 wherein said basin contains two steps for keeping said at least one cassette off of the floor of said basin wherein a step is located at each lateral end of said basin.

11. The system of claim 1 wherein an indicator mark regulates the positioning of said at least one cassette within said basin.

12. The system of claim 1 wherein said first electrode is a cathode electrode connected to a wiring arrangement providing a wire to the top of said upper buffer chamber and a wire to the bottom of said upper buffer chamber.

13. The system of claim 1 wherein said second electrode is an anode electrode located on the base of said frame assembly.

14. The system of claim 1 wherein said lower buffer chamber has a fill-line indicator for regulating the volume of electrolyte solution to be contained in said lower buffer chamber.

15. The system of claim 14 wherein the depth of said lower buffer chamber is sufficient to contain the volume of said electrolyte solution up to the fill-line plus the volume of an electrolyte solution placed into said at least one upper buffer chamber.

16. The system of claim 1 wherein at least one knobbed screw is used to tighten said at least one clamp mechanism.

17. The system of claim 1 wherein said at least one spring post located on said frame assembly offers resistive force against said at least one clamp mechanism.

18. The system of claim 1 further comprising at least one heat exchanger having an inlet port for coolant flow, compartments defining a flow path for coolant flow sandwiched between two heat-conductive plates, and an outlet port for coolant flow.

19. The system of claim 18 wherein said heat exchanger is located in the center of said frame assembly.

20. The system of claim 18 wherein said flow path for coolant flow is serpentine.

21. The system of claim 18 wherein said heat-conductive plates are composed of an electrically insulating material.

22. The system of claim 18 wherein said coolant is water.

23. The system of claim 1 further comprising a cover.

24. The system of claim 23 wherein said cover has a horizontal groove or ridge on each of the vertical side ends of said cover.

25. The system of claim 23 wherein said cover encloses said frame assembly within said lower buffer chamber.

26. The system of claim 23 wherein said cover contains receiving members for said first electrode and said second electrode, said receiving members having insulated electrical connecting means for attaching said system to an electrical current source.

27. The system of claim 23 wherein said cover has at least one hole on the top surface of said cover for receiving at least one small post projecting upwards from said frame assembly, said post serving to facilitate thumb placement during removal of said cover.

28. The system of claim 1 further comprising a solid rectangular plate for use when a single cassette is clamped to said frame assembly, said solid rectangular plate positioned on the opposite side of said frame assembly from that occupied by said single cassette, to complete the formation of said upper buffer chamber.

29. A method for providing at least one separation medium within a system for performing electrophoresis comprising the steps of:
  (a) providing at least one cassette for containing at least one separation medium, said cassette comprising (i) a first plate and a second plate, (ii) a space for containing said separation medium, between said first plate and said second plate, said cassette having an open top and an open bottom;
  (b) positioning said at least one cassette on a frame assembly for receiving said at least one cassette, said frame assembly having (i) at least one clamp mechanism for pressing said at least one cassette against said frame assembly in a substantially vertical position thereby forming a fluid-tight seal between said first plate and said frame assembly and defining at least one upper buffer chamber, (ii) a base comprising a platform extending beyond said at least one cassette when said cassette is clamped in position on said frame assembly, said platform having at least one basin for receiving the open bottom of said at least one cassette and for containing a solution capable of plugging the bottom of said cassette, (iii) at least one first electrode for said upper buffer chamber, and (iv) at least one second electrode for a lower buffer chamber;
  (c) filling said at least one basin with said solution capable of plugging said bottom of said cassette; and
  (d) pouring a solution capable of serving as said separation medium into said space between said first plate and second plate of said at least one cassette after said bottom of said cassette is plugged.

30. The method of claim 29 wherein said frame assembly is placed into said lower buffer chamber prior to pouring said solution capable of serving as said separation medium into said cassette.

31. The method of claim 29 wherein said frame assembly is placed into said lower buffer chamber after pouring said solution capable of serving as said separation medium into said cassette.

32. The method of claim 29 wherein said first plate and said second plate are flat and generally rectangular.

33. The method of claim 29 wherein said first plate and said second plate are glass.

34. The method of claim 29 wherein said first plate and said second plate are at least 20 cm by 20 cm.

35. The method of claim 29 wherein said first plate bears a longitudinal notch along a top edge to facilitate contact between said separation medium and a solution of electrolytes.

36. The method of claim 29 wherein said first plate and said second plate are separated by two strips of dielectric material placed along each vertical side of said first plate and between said first plated and said second plate.

37. The method of claim 29 wherein said clamp mechanism also presses said first plate and said second plate together.

38. The method of claim 29 wherein said solution for plugging said bottom of said cassette is electrically conductive.

39. The method of claim 29 wherein said solution for plugging said bottom of said cassette comprises agarose.

40. The method of claim 29 wherein said solution for plugging said bottom of said cassette comprises ethylene vinyl acetate doped with carbon.

41. The method of claim 29 wherein said solution for plugging said bottom of said cassette comprises a non-solidifying solution capable of presenting said at least one separation medium with a resistive force greater than the hydrostatic pressure of said separation medium at a height of said first plate.

42. The method of claim 41 wherein said non-solidifying solution comprises glycerol.

43. The method of claim 29 wherein said at least one separation medium remains in a liquid state.

44. The method of claim 29 wherein said at least one separation medium comprises a gel.

45. The method of claim 29 wherein the temperature of said at least one separation medium is controlled by at least one heat exchanger having an inlet port for coolant flow, compartments defining a flow path for coolant flow sandwiched between two heat-conductive plates, and an outlet port for coolant flow.

46. A method for performing vertical electrophoresis comprising:
  (a) providing a separation medium in an electrophoresis system, said system comprising (i) at least one cassette containing two spaced plates, and (ii) a frame assembly for holding said at least one cassette in a substantially vertical position, said frame assembly containing at least one cathode electrode and at least one anode electrode, and said frame assembly further providing a base with at least one basin containing a solution capable of plugging a bottom opening of said cassette, wherein said separation medium is contained between said two spaced plates and wherein said separation medium is provided after the bottom opening of said cassette is plugged;

(b) applying at least one sample to be separated to the top of said separation medium wherein contact is made between said sample and said separation medium; and (c) separating molecular components of said sample by providing an electrical current through said separation medium.

47. The method of claim 46 wherein said solution capable of plugging said bottom opening of said cassette is electrically conductive.

48. The method of claim 46 wherein said solution capable of plugging said bottom opening comprises agarose.

49. The method of claim 46 wherein said solution capable of plugging said bottom opening comprises ethylene vinyl acetate doped with carbon.

50. The method of claim 46 wherein said solution capable of plugging said bottom opening comprises a non-solidifying liquid capable of providing a greater resistive force than that provided by said separation medium at the height of said cassette.

51. The method of claim 50 wherein said non-solidifying plugging solution comprises glycerol.

52. The method of claim 50 wherein said separation medium is a gel.

53. The method of claim 46 wherein said separation medium contains acrylamide.

54. The method of claim 46 wherein said separation medium contains agarose.

55. The method of claim 46 wherein said separation medium is a liquid.

* * * * *